April 5, 1960 F. W. ANDERSON Plant Pat. 1,929

NECTARINE TREE

Filed Aug. 14, 1959

WITNESS

Addison E. Avery

INVENTOR

Frederic W. Anderson

Webster & Webster

ATTYS.

United States Patent Office

Plant Pat. 1,929
Patented Apr. 5, 1960

1,929

NECTARINE TREE

Frederic W. Anderson, Merced, Calif., assignor to Stark Bro's Nurseries and Orchards Co., Louisiana, Mo., a corporation of Missouri Application August 14, 1959, Serial No. 833,900

1 Claim. (Cl. 47—62)

This invention relates to a new and distinct variety of nectarine tree which bears freestone fruit having yellow flesh shading to red adjacent the stone; the skin of the fruit being yellow partially overspread with red. The variety is of the type embraced by group 118 of the classification by Caillavet and Souty, Monographie des Principales Variétés de Pêchers, 1950 edition, page 46.

As compared with the Sun Grand (United States Plant Patent No. 974)—which, at present, is the most extensively commercially grown freestone nectarine in California—the present variety has leaves with reniform instead of globose glands; has non-showy instead of showy flowers; and bears fruit which is of an average larger size, is more nearly globose in shape, ripens approximately one week earlier, and has a darker red exterior color.

The present variety of nectarine tree was originated by me in my experimental orchard located near Merced, California, and is a cross between the Sun Grand nectarine and a commercially unnamed nectarine, but which is identified in my experimental records as the Anderson B-11 (unpatented).

Subsequent to origination of the variety I asexually reproduced it in my experimental orchard, located as aforesaid, by topworking on mature orchard trees; such reproductions having run true in all respects.

Figure 1:
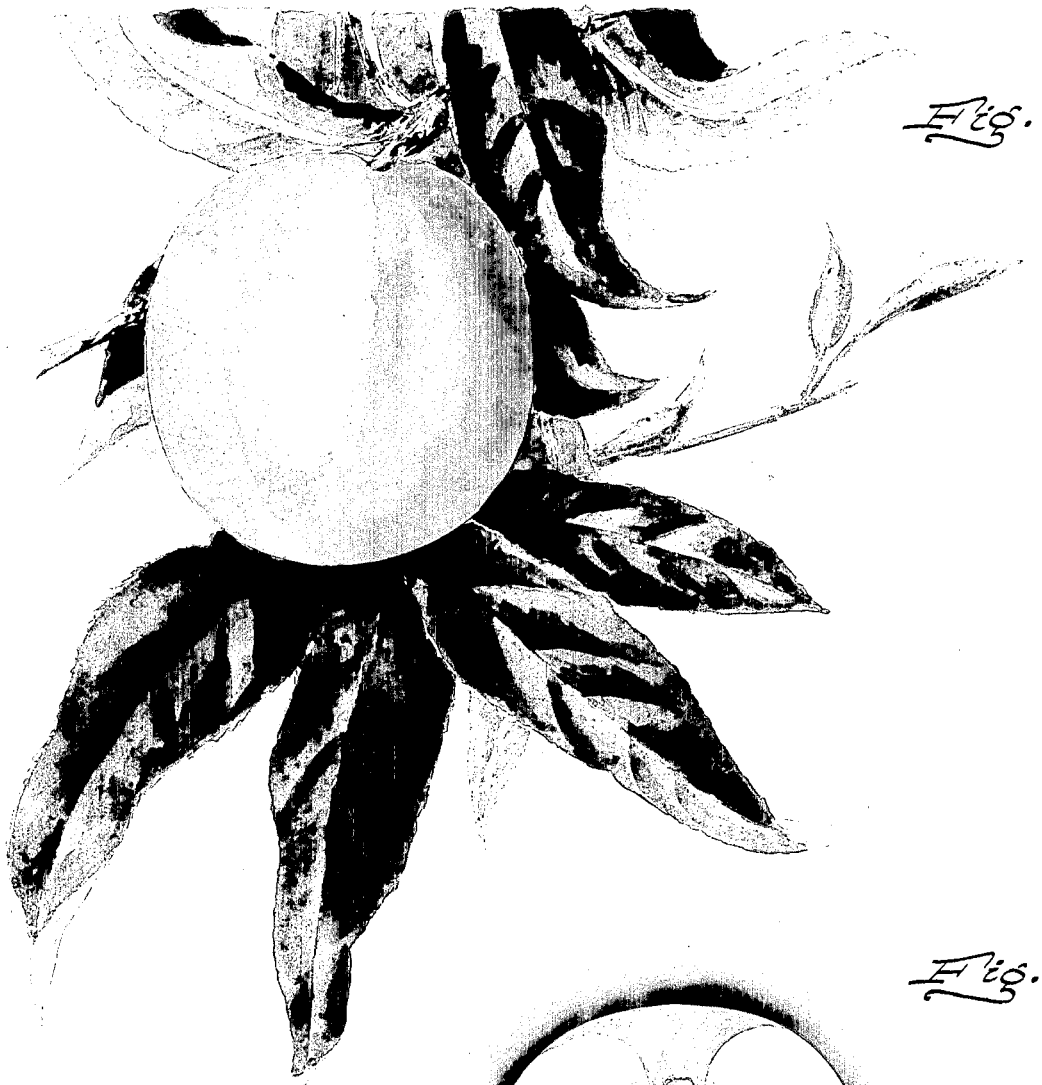
Fig. 1 is an elevation showing one of the nectarines, together with twigs and leaves.
Figure 2:
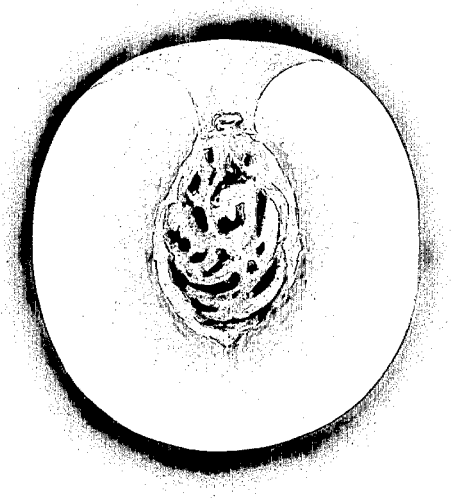
Fig. 2 is a sectional elevation of one of the nectarines with the stone remaining in place.

Referring to pomological details of this new and distinct variety of peach tree and its fruit, the following is an outline description thereof; all major color plate identifications being by reference to Maerz and Paul Dictionary of Color:

Tree:
- *Size.*—Large to medium.
- *Vigor.*—Vigorous.
- *Production.*—Productive.
- *Bearing.*—Regular bearer.

Trunk: Size—stocky.
Branches: Size—stocky to medium.
Leaves:
- *Size.*—Large to meduim.
- *Margin.*—Glandular; crenate.
- *Petiole.*—Medium length.
- *Glands.*—Reniform. Position—usually two on petiole and two or more on blade.
- *Color.*—Top side—medium green (22-L-7). Under side—lighter green (22-K-6).

Flower buds: Size—large.
Flowers: Blooming period (1958).
- *Date of first bloom.*—March 2nd.

- *Date of full bloom.*—March 12th. Medium as compared with other varieties.
- *Size.*—Medium.
- *Type.*—Non-showy.

Fruit:
- *Maturity when described.*—Eating ripe—July 9, 1958.
- *Date of first picking.*—July 1, 1958.
- *Date of last picking.*—July 10, 1958.
- *Size.*—Uniform to variable; large. Average diameter axially—2⅝". Average transversely in suture plane—2¾".
- *Form.*—Symmetrical; globose.
- *Suture.*—Distinct; extends from base to beyond apex, with slight depression beyond pistil point.
- *Ventral surface.*—Rounded slightly.
- *Lips.*—Equal to unequal.
- *Cavity.*—Circular.
- *Base.*—Rounded.
- *Apex.*—Short.

Skin:
- *Thickness.*—Medium.
- *Texture.*—Medium.
- *Tendency to crack.*—None noted.
- *Color.*—Yellow (9-L-5), partially overspread with red (2-J-11 to 5-L-5).

Flesh:
- *Texture.*—Firm; meaty; melting.
- *Ripens.*—Even.
- *Flavor.*—Subacid.
- *Eating quality.*—Good.
- *Color.*—Yellow (9-L-5), shading to red (2-J-11 to 1-L-4) toward the stone, with darker red (4-L-8) closely adjacent thereto.

Stone:
- *Type.*—Free; parts from flesh smoothly.
- *Size.*—Medium.
- *Form.*—Oblong.
- *Base.*—Straight.
- *Apex.*—Acute.
- *Sides.*—Equal to unequal.
- *Ridges.*—Rounded to jagged.
- *Pits.*—Elongated.
- *Ventral edge.*—Thin.
- *Dorsal edge.*—Full.
- *Tendency to split.*—Slight.
- *Color.*—Brown (14-E-12).

Use: Market.
Keeping Quality: Good.
Shipping quality: Good.

The tree and its fruit herein described may vary in slight detail due to climatic and soil conditions under which the variety may be grown; the present description being of the variety as grown in the Central Valley of California.

The following is claimed:

A new and distinct variety of nectarine tree, as illustrated and described, which bears freestone fruit having yellow flesh shading to red adjacent the stone, and skin which is yellow partially overspread with red; characterized—in comparison with the Sun Grand nectarine—by leaves having reniform instead of globose glands, by non-showy instead of showy flowers, and by fruit which is of average larger size, is more nearly globose in shape, ripens approximately one week earlier, and has a darker red exterior color.

No references cited.